United States Patent [19]

Bianchi et al.

[11] Patent Number: 5,084,147
[45] Date of Patent: Jan. 28, 1992

[54] PROCESS OF SYNTHESIS OF ORGANIC SUBSTANCES BY AN INDIRECT ELECTROCHEMICAL ROUTE WITH A REDOX SYSTEM IN THE SOLID STATE

[75] Inventors: Giuseppe Bianchi, Piazzle Libia, 1; Franco Valsecchi, Via Diaz, 5, Cernusco Sul Naviglio; Giovanni Burei, all of Milan, Italy

[73] Assignees: Giuseppe Bianchi, Piazzale Libia; Franco Valsecchi, Milan; Enichem Synthesis S.p.A., Ruggiero Settimo 55 Palermo, all of Italy

[21] Appl. No.: 295,106

[22] Filed: Jan. 6, 1989

[30] Foreign Application Priority Data

Jan. 8, 1988 [IT] Italy .................. 19027 A/88

[51] Int. Cl.5 ............................................. C25B 3/02
[52] U.S. Cl. ........................................ 204/72; 204/78
[58] Field of Search ................................. 204/78, 72

[56] References Cited

U.S. PATENT DOCUMENTS

| | | | |
|---|---|---|---|
| 3,953,305 | 4/1976 | Connolly | 204/78 |
| 4,411,746 | 10/1983 | Degner et al. | 204/78 |
| 4,488,944 | 12/1984 | Stutts et al. | 204/79 |
| 4,496,440 | 1/1985 | Campbell et al. | 204/78 |
| 4,596,638 | 6/1986 | Trocciola et al. | 204/73 R |
| 4,640,750 | 2/1987 | Blickle | 204/79 |
| 4,692,227 | 9/1987 | Spotnitz et al. | 204/78 |
| 4,701,245 | 10/1987 | Kreh | 204/78 |

FOREIGN PATENT DOCUMENTS 0129790 7/1984 Japan.

Primary Examiner—John F. Niebling
Assistant Examiner—Steven P. Marquis
Attorney, Agent, or Firm—Bucknam and Archer

[57] ABSTRACT

A process of oxidation or reduction of organic substrates by an indirect electrochemical route is described. During oxidation, the electrochemical stage produces a metallic oxide having higher valence such as $RuO_2$, NiOOH, which is applied to an inert conductor support. The supported metallic oxide of higher valence is separated from the aqueous electrolyte and is then placed in contact with the pure organic material to be reacted on. The metallic oxide in this manner is reduced to a lower valence and is subjected to a new electrochemical oxidation after the residues of the organic material are removed. The process consists of a cyclic repetition of these stages. The process of reduction of organic substrates is analogous and is carried out by means of the hydrogen of hydrides formed through a cathodic charge by electrolysis of an aqueous solution.

17 Claims, 6 Drawing Sheets

Figure 2:
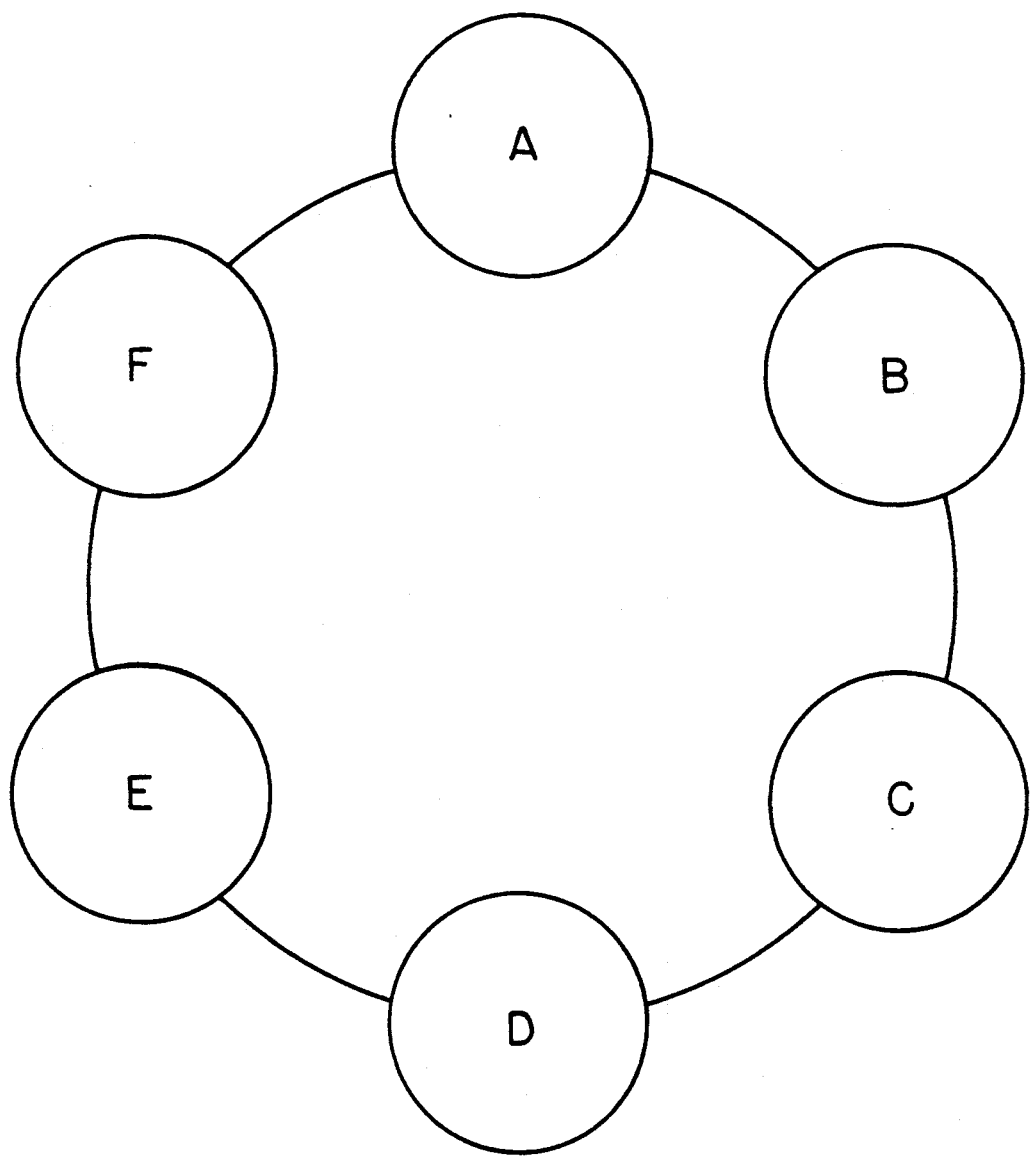

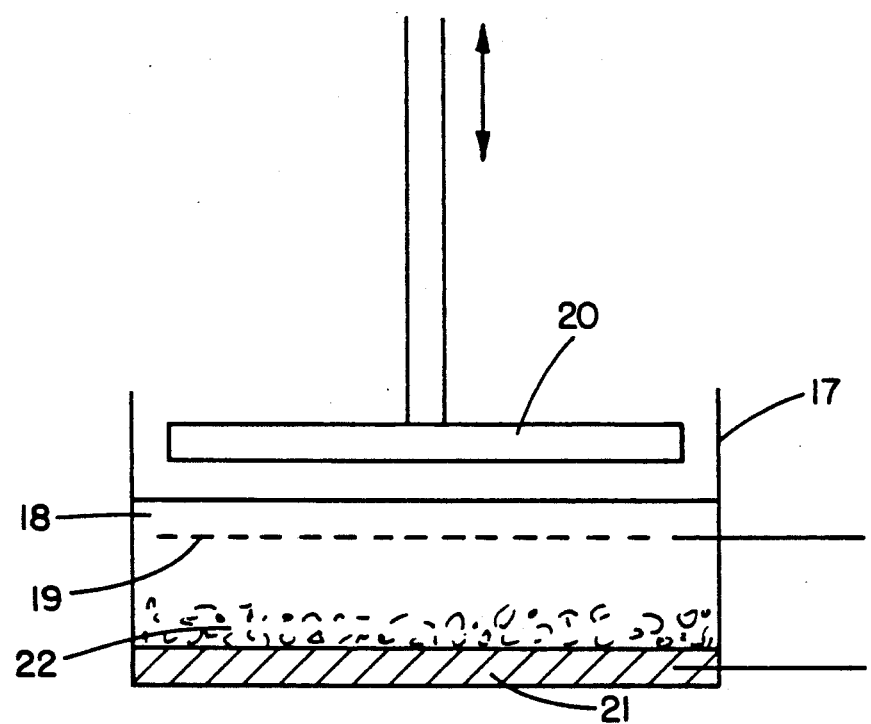
FIG. 2,a

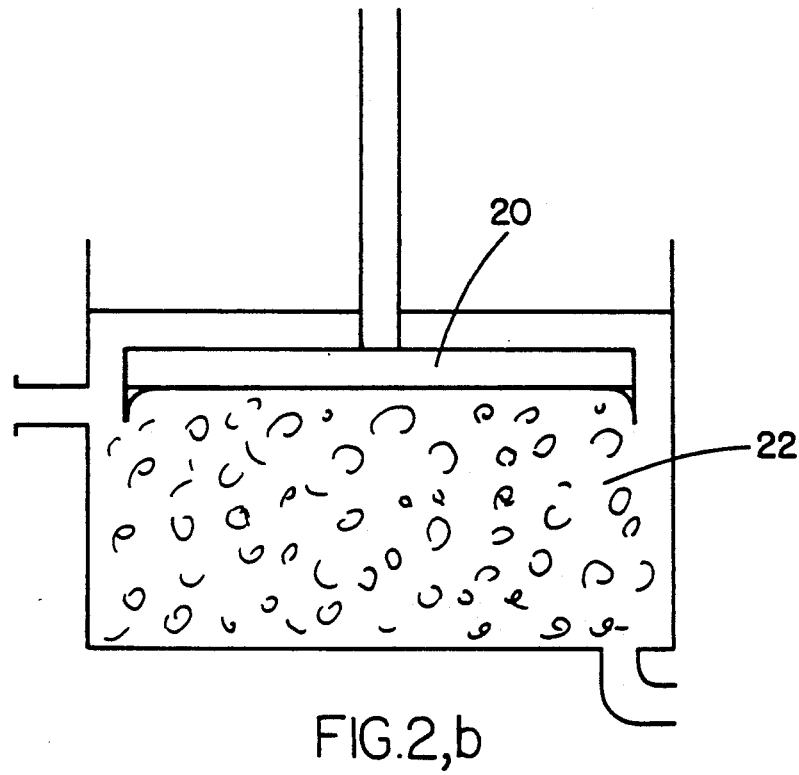
FIG.2,b
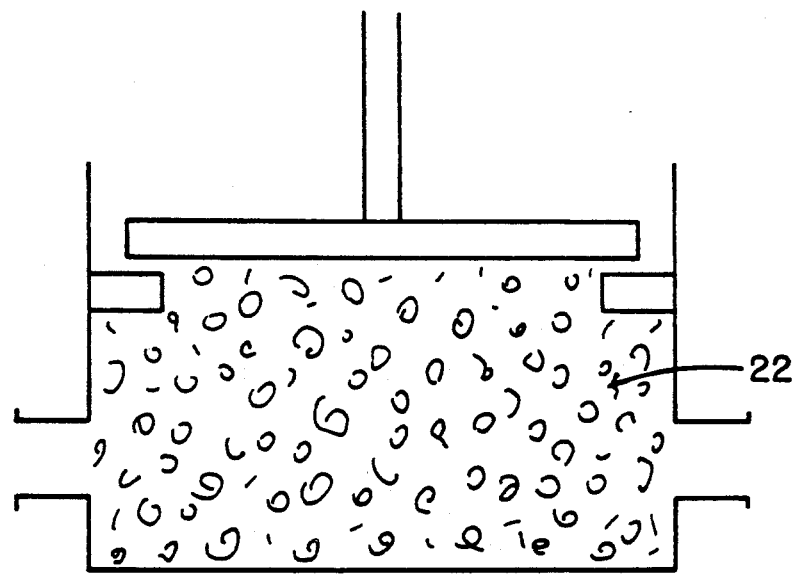
FIG.2,c

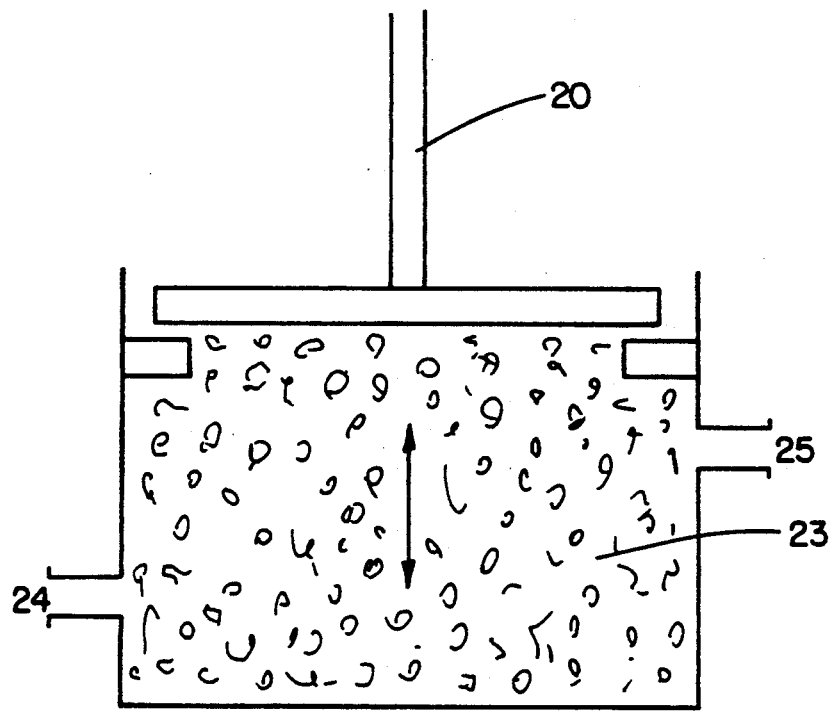
FIG.2,e
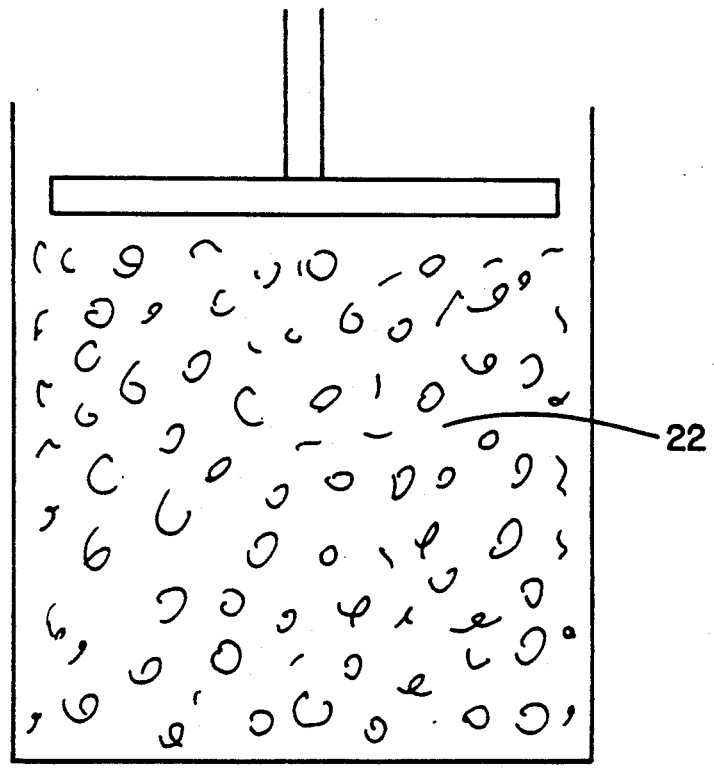
FIG.2,d

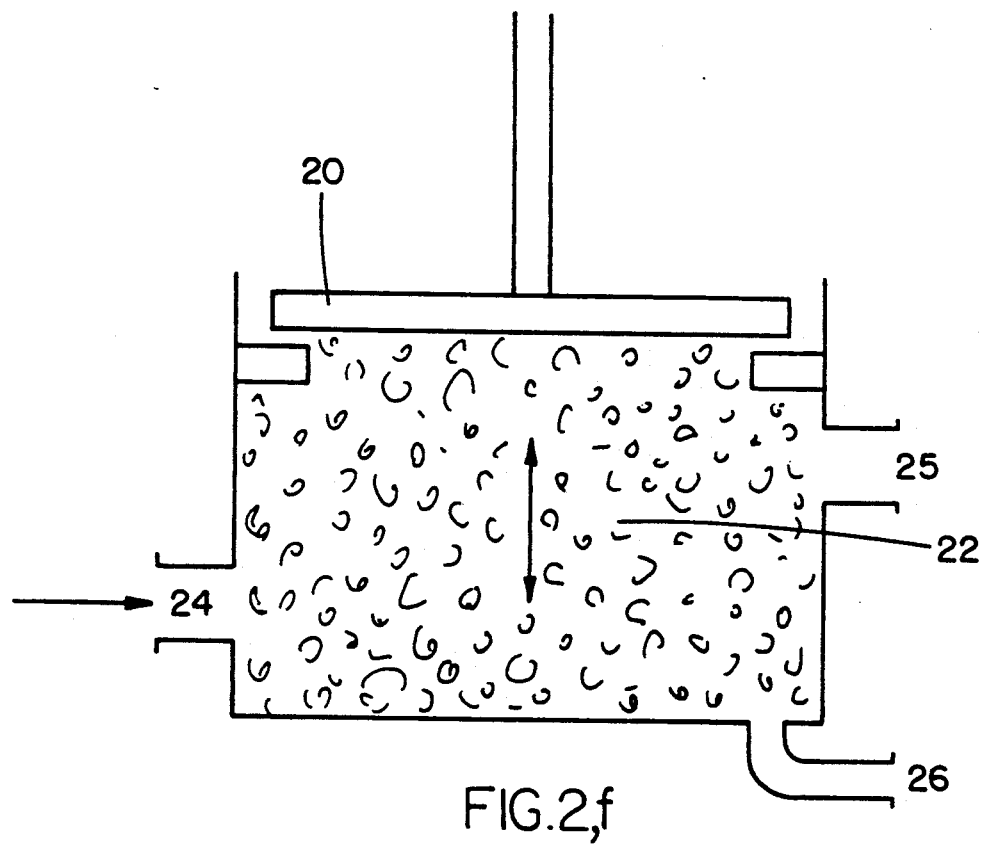
FIG.2,f

PROCESS OF SYNTHESIS OF ORGANIC SUBSTANCES BY AN INDIRECT ELECTROCHEMICAL ROUTE WITH A REDOX SYSTEM IN THE SOLID STATE

The present invention relates to a process of synthesis of organic substances by an indirect electrochemical route with a redox system in the solid state.

The direct production by the electrochemical route of organic substances presents a fundamental difficulty due to the fact that the electrochemical properties of the electrolyte, first of all the electric conductivity must be rendered compatible with the chemical properties, such as the solubility of the substrate and the organic product. The adoption of tetraalkyl ammonium salts is typical as in the case of the synthesis of adiponitrile by hydrodimerization of acrylonitrile. The electrolyte must be prepared specially for the particular organic reaction involved and must be separated from the organic substrates with recycling downstream of the electrolytic cell. The installation required may amount to 70–80% of the entire investment. In addition, it is almost impossible to build installations for a variety of purposes because of the specificity of the electrolyte and the consequent specificity of the installation of separation downstream.

The direct synthesis by the electrochemical route by an anodic reaction presents the additional difficulty that the oxidation must be stopped at the desired level without degradation of the substrate and without formation of undesirable heavy products. These heavy products contaminate the anode and may require periodical cleaning.

In a relatively more recent time there have been described, particularly for the oxidative reactions, indirect electrochemical processes in which the oxidation of the organic substrate is carried out by a reagent which is regenerated by the electrochemical route. For instance, N. Stol, K. Kramer, L. Ponto and P. Robertson, Alch E. Symposium Series N. 185. 75, 45 (1979), describe a process based on a cell in which a salt of cerium of valence $+3$ is oxidized to a salt of cerium of valence $+4$ by conventional electrolysis of an aqueous solution. The solution of the salts of cerium with the higher valence is then introduced into a reactor in which it reacts either in an homogeneous phase or in a heterogeneous phase with respect to the solubility, with the organic substrate and in which it oxidizes the substrate up to the level corresponding to the utilized redox pair, for instance, $Ce^{4+}/Ce^{3+}$ and, therefore, it is reduced to a salt of cerium of the lower valence of $+3$. At the exit of the reactor the electrolytic solution and the organic material are separated and are introduced respectively into an electrolytic cell and into an apparatus for the purification of the organic substances. The operation in two separate stages, one electrochemical for the regeneration of the redox system and the other for the organic reaction, diminishes the problems of conductivity, solubility, stability, etc., but still maintains the difficulties resulting from the specific processes of separation and purification of the electrolyte, in addition to the difficulties of separation of the organic substances which did not react and purification of the final product. Problems resulting from the organic substance being carried into the electrolytic cell with consequent contamination of the electrodes make the treatment for the recirculation of the electrolytes critical and require investments in this part of the installation, which result to be substantial with respect to the overall investments. In addition, the reaction between the oxidizing electrolytic solution and the organic substrate in the reactor occurs at a sufficient rate only if the organic substrate which is scarcely soluble is effectively dispersed in the aqueous phase. The functioning of the reactor, therefore, absorbs a quantity of energy which is not negligible.

The possibility of oxidizing an organic substance by reaction with a metallic oxide, for instance, NiOOH, $Ag_2O$, $MnO_2$ has been known for a long time. This route, up to the present time, presents an interest which is limited to preparations on a laboratory scale because of the cost of the reagents, the quality and stability of the same reactants which vary greatly according to the manner of preparation and the ecological problems connected with the disposal of the salts of heavy metals.

The object of the present invention is to provide a process of organic synthesis by the indirect electrochemical route in which the reduction or oxidation of the organic substance is carried out by means of an heterogeneous reaction. When oxidation is desired the process utilizes a redox system based on oxides in which both the oxide with the metal in the higher valence, as well as the oxide with the metal in the lower valence are in the solid state. When the process is carried out for a reduction, the process utilizes hydrides and will be described hereinbelow. The oxidative redox system is characterized by the fact that a cycle is provided between the anodic conditions of the electrolytic cell in which the oxide with the metal in the higher valence is formed and the conditions of the reactor in which the organic substance is oxidized at the expense of the oxide. The reduced oxide with the metal in the lower valence is reintroduced in the cell and then reenters the cycle in the form of the oxide with the higher valence.

The specificity of the invention resides in the fact that the indirect electrochemical process is characterized by the following:

1. The use of a redox system in the solid state in which the separations between the electrolyte and the organic substrate occur by a simple drainage, filtration or centrifugation;
2. The redox system in the solid state after separation of the electrolyte as mentioned in item 1 hereinabove optionally is washed with solvents or in a vapor stream;
3. The organic substance which is produced, which could be a high boiling substance, is separated from the redox system in the solid state, by steam distillation or distillation under vacuum;
4. The organic reaction may be carried out also with a substrate in the gaseous form and may give a product in the gaseous form;
5. The organic reaction may be carried out over broad ranges of temperature and pressure because it is carried out after the electrolyte has been removed.

The redox system in the solid state is characterized by the following:

1. By the chemical properties: oxidation-reduction potential, thermal stability, stability to water or solvents;
2. Electrical properties, particularly electronic conductivity;
3. Surface properties, surface area and electric charge accumulated by the redox system per unit of geometric surface expressed in equivalents/$m^2$;

4. Structural properties and their modifications in the recycling between the higher valence and the lower valence;
5. Mechanical properties: adherence to the metallic base and resistance to wear and impact;
6. Catalytic properties in the channeling the organic reaction of oxidation or reduction.

Among the redox systems in the solid state one can mention, in addition to those already mentioned, other systems which have been developed more recently and originally intended for other applications ("Electrodes of Conductive Metallic Oxide," Part 1 and B-S. Editor Trasati; Elsevier: Amsterdam 1981)

The system supported on titanium $RuO_2$-$TiO_2$ may be prepared by thermal decomposition of ruthenium chloride and titanium chloride according to methods amply described in the literature. By depositing layers for a total thickness of $2\mu m$ containing 10-15 g of $RuO_2/m^2$, the redox system accumulates a charge of about 1,000 Coul/$m^2$ when it is recycled in an acidic solution between a potential of 0.4V and 1.2V (on a hydrogen scale).

With a structure of $1m^2$ one can oxidize, for instance, 0.37 g of isobutanol to methylethylketone according to the following reaction:

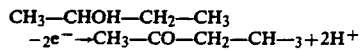

Another redox system recently studied is the spinel $NiCo_2O_4$ deposited on metallic surfaces by thermal decomposition using solutions of nitrates as starting materials. With deposits of thickness of $3\mu m$ corresponding to about 18 $g/m^2$, the redox system presents in an alkaline solution an anodic peak of about 1.43V on a hydrogen scale with an accumulation of about 1,000 Coul/$m^2$. With $1m^2$ of this system one can, for instance, oxidize 0.23 g of toluene to benzaldehyde.

Figure 1A:
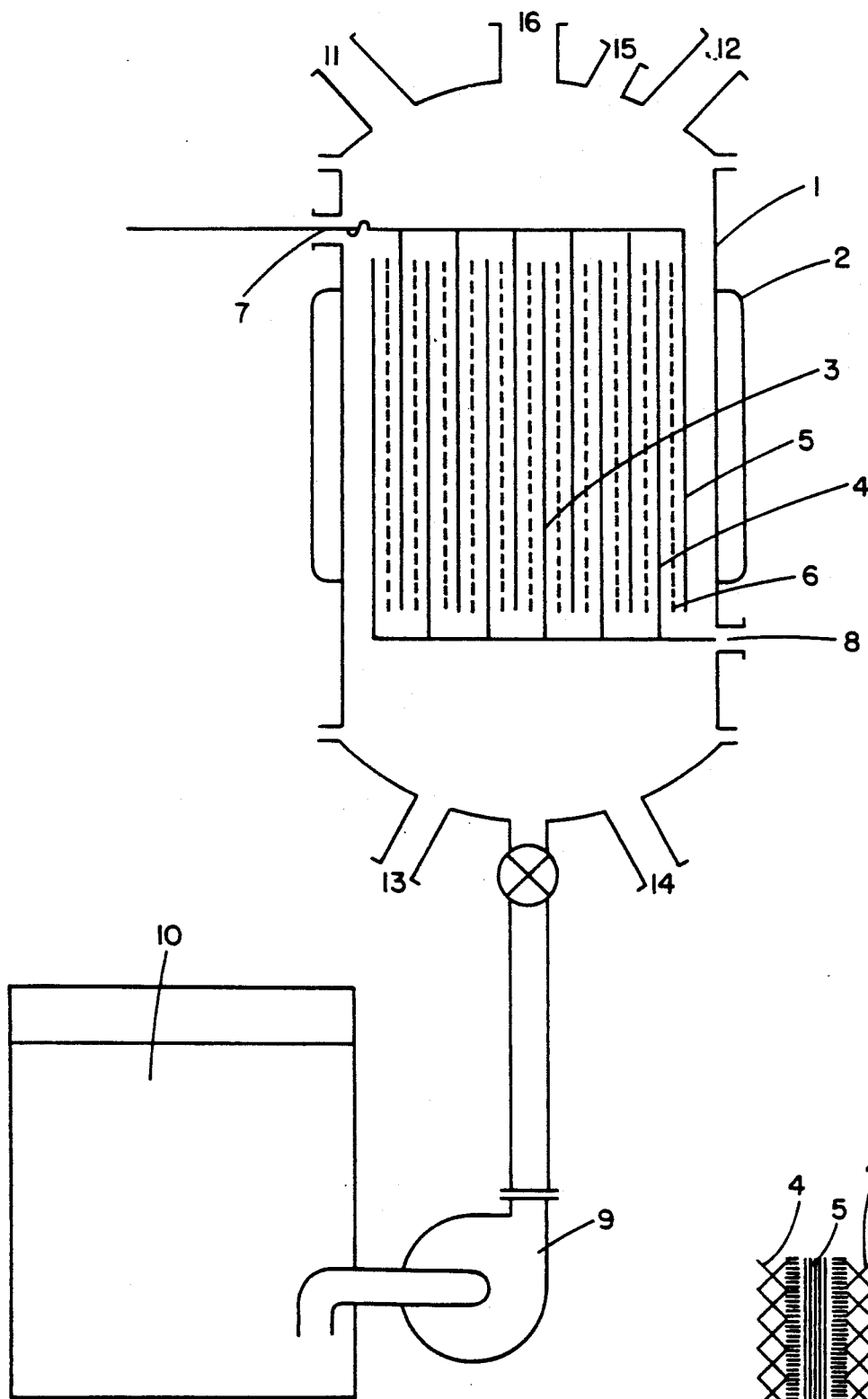

The particular feature of the process which is the abject of the present invention is illustrated in the accompanying figures and will appear clear by the description in connection with the figures. FIG. 1a illustrates a reactor with a fixed bed which is also used for the electrochemical reaction;

FIG. 1a illustrates the electrode pack;
FIG. 2 illustrates a reactor with a moving beg;
FIGS. 2 a-f illustrate the installation in the form of a carousel connected with a magnetic plate.

FIG. 1a shows the reactor with a fixed bed being used when the process is carried out for an electrochemical oxidation by the indirect route. The process is analogous when a reduction process is being carried out. Numeral 1 is a container provided with a jacket 2 for heating or cooling. An electrode pack 3 is placed within the container, the pack consisting of alternate cathodes 4 and anodes 5 between which are inserted the separators 6. All the anodes are connected to an anodic bar which goes through the wall of the container by means of an insulated passage 7. In a similar manner the cathodes ground are connected in 8.

FIG. 1a' illustrates in detail the electrode pack 3. The cathodes 4 consist of an expanded net of wide mesh of stainless steel or copper, copper alloys, etc. The anodes 5 occupy a great surface and consist of a pack of nets of nickel superimposed and head lap welded among themselves and have in the center a stretched net or a net with a wide mesh. Alternatively, the anodes may be made of porous plastic material with open cells such as a polyurethane foam with a surface deposit of metal, for instance, nickel obtained by the electroless and galvanic route. Separators 6 are nets or microporous diaphragms of polyethylene or analogous material.

The reactor operates alternately as an electrolytic cell and as the reactor for oxidation of the organic substrate. In the electrochemical stage the reactor is filled with an aqueous solution which in the case described herein is an alkaline solution, for instance 10% KOH which is introduced from the reservoir 10 by means of pump 9. The anodic bars and the ground of the container 1 are connected to a generator of direct current which is not shown in the figure and which delivers a current in the range of 100-3,000 A/$m^2$ of anodic pack. Hydrogen is evolved on the cathodes. On the anodes NiO(OH) is formed by oxidation of the Ni(OH)$_2$ present. Simultaneously oxygen is evolved. The cover of the reactor is flushed with air or nitrogen through the openings 11-12 in order to be outside of the limit of explosiveness of the mixture $H_2$—$O_2$.

When the desired quantity of NiO(OH) is formed on the nickel nets (generally 3,000 coulombs/$m^2$), the current is interrupted, the solution of KOH is reintroduced in the reservoir 10, the electrode pack is washed, if required, with distilled water or with vapor introduced through the inlet 13 and the water used for the washing or formed by condensation is eliminated through an outlet at the bottom, not shown in the figure. After the washing, the pack of electrodes may, if required, be dried by heating by letting warm air go through the Jacket 2.

In the reactor arranged in this manner is introduced the liquid organic substrate which is oxidized by means of NiO(OH) which in turn is reduced to Ni(OH)$_2$ and remains on the anode surface ready for the subsequent electrochemical cycle. The organic substance may be introduced in the reactor through the inlet 14 and may be removed through outlet 15. Alternately, the organic substance may be kept in the reactor for a definite period of time and may be loaded and unloaded through the outlet at the bottom 14.

After the oxidation stage is terminated, the reactor is unloaded, washed with a solvent or preferably in a vapor current to remove from the electrodes the deposits of heavy organic products which may eventually have been formed, and the reactor is ready for the subsequent electrochemical cycle. Alternately, the organic substance may be introduced into the reactor in the form of a vapor, and the product may be removed in the form of vapor through the outlet 16 or in the liquid form or in the solid form which has impregnated the anodes and may be removed by steam distillation.

Several variations are possible with respect to the shape of the container and the shape of the pack of electrodes. A preferred embodiment is an anodic pack consisting of nets of titanium activated with $RuO_2$-$TiO_2$ and which utilizes an aqueous solution of 5-10% $H_2SO_4$. The electrochemical stage of charging the redox system and introduction of the solution may last one minute. The stage of reaction of the organic substrate, removal of the solution and washing may last a few minutes with a value of about ten complete cycles for each hour. With an electrode section of $1m^2$ ($1m \times 1m$) and anodic packs consisting of four nets with a fine mesh and a central net with a wide mesh for a surface of $5m^2$ with an overall thickness of 40 mm of the electrode block (cathode, separator, pack of anodes and separator) in a $1m^3$ there are contained $125m^2$ of anodic surface which, in the case of electrodes covered with a film of $RuO_2$-$TiO_2$, correspond to 125,000 coulombs, equivalent to 1.25 equivalents. With 10 cycles/h the reactor of 1m³ is capable of oxidizing an organic substance with a charge corresponding to 12.5 equivalents. The total amount of ruthenium being used results to be about 1.5 kg/m³ of the reactor.

By introducing into the reactor during the chemical phase pure isobutanol, there is obtained methylethylketone with a yield based on isobutanol reacted equal to 90% and with an overall electric yield of 70% (1.8 kwh/kg of reacted isobutanol with an electrolysis potential equal to 2.5V).

After fifteen days of operation no substantial contamination of the electrodes is noted and the electrical conversion yield is kept constant. The separation of methylethylketone and isobutanol does not present particular difficulties, because this separation is carried out by a simple distillation of the mixture which contains 40% by weight of methylethylketone; the organic mixture is contaminated by small traces of sulfuric acid used as the electrolyte during the electrochemical reoxidation of the electrolytes. In order to achieve this optimum result, the pack of electrodes is washed with distilled water after removal of the acidic electrolyte and warm air is then blown through it.

It has been found that the distilled water used for washing may be introduced in a reservoir and may be used for many cycles without affecting the process, thus permitting to minimize the amount of effluents during the operation.

After the oxidation stage and after the organic phase is removed, the residues of organic material which are formed on the surface of the electrodes are removed by means of a stream of warm air, are recovered downstream by condensation and are recycled during the organic phase of the reaction.

In this connection a particularly interesting application is the oxidative purification of products obtained by chemical synthesis which are not sufficiently pure because they contain still oxidizable impurities. In an analogous fashion, one can proceed with a process of reduction for the purification of products which contain reducible impurities.

With reference to oxidative treatments or reductive treatments which have been carried out by addition of oxidizing or reducing agents, the process according to the present invention has the advantage of being "clean" and has great potentialities of choice of the redox system in the solid state so that it is rendered suitable for each specific requirement of compatibility for the characteristics of the impurities present with respect to the impurities of the product which is desired.

The system is easily adaptable to different processes. For instance, after one substitutes the pack of electrodes covered with $TiO_2$-$RuO_2$ with a pack of anodes made of nickel and cathodes made of stainless steel described hereinabove, one introduces into the reactor isoamyl alcohol and follows the same procedure of intermediate washing as described hereinabove. The reaction proceeds according to the following scheme:

The isovaleric acid is obtained with a yield based on the amount of isoamyl alcohol used equal to about 70% and with an overall electric yield equal to 50%.

In an analogous manner β-chloropropionaldehyde is introduced into the reactor using the same pack of anodes of nickel and cathodes of stainless steel. The reaction takes place according to the following scheme:

The B-chloropropionic acid which is formed is distilled under vacuum; the yield is 65% based on the aldehyde starting material. An oxidation has been described in the literature by the chemical route by means of fuming nitric acid.

The oxidation of toluene with nitrosylsulfuric acid gives a mixture which contains, in addition to the toluene starting material, 30% of benzaldehyde also 30% of benzoic acid and 12% of benzyl alcohol. When the mixture is subjected to a fractional purification the major part of the toluene, benzaldehyde and benzyl alcohol are removed, thus obtaining benzoic acid which is still contaminated with 1.5-2.0% of benzyl alcohol and benzaldehyde. This benzoic acid of melting point 122° C., impure, in the molten state, is subjected to a process of oxidation by the electrochemical indirect route according to the present invention utilizing the redox system previously described $RuO_2$-$TiO_2$ supported on titanium. Pure benzoic acid is obtained according to the reaction scheme hereinbelow:

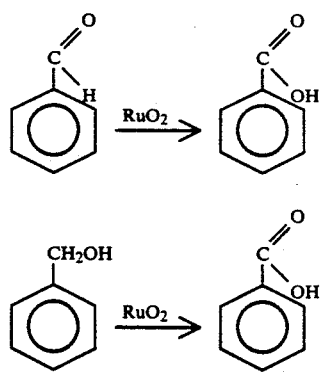

In an analogous manner, one obtains p-chlorobenzoic acid in the pure state by subjecting to oxidative purification the impure acid which contains as impurities the p-chloro benzaldehyde and p-chloro benzyl alcohol in the amount each of 1% according to the reacting scheme hereinbelow:

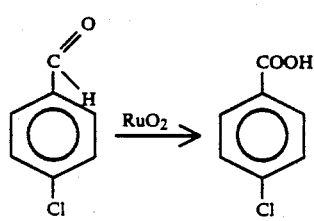

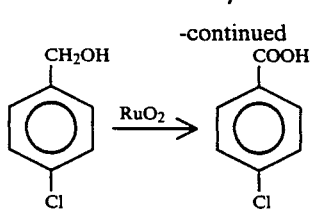

A few tests have been carried out oxidizing p-chloro benzylalcohol to p-chloro benzaldehyde by means of $MnO_2$. There are used seven expanded plates of titanium which have a total surface of 1,200 cm$^2$ with reference to the two surfaces and which are used as the anode in a aqueous solution of $MnSO_4.H_2O$ (140 g/l) and $H_2SO_4$ (50 g/l) at a temperature of 60° C. A nickel cathode is used. The current is 2.5 A (20 A/m$^2$) for a period of three hours. The amount of electricity being circulated is 0.28 equivalent. In this manner there are deposited 22 g of $MnO_2.nH_2O$ which correspond to a thickness of 35 μm. The plates which are prepared in this manner are washed, dried with warm air and then are caused to react with 8.93 g. (6.27·10$^{-2}$ mol) of p-chloro-benzyl alcohol dissolved in toluene in the concentration of 5 g/l. By operating at 25° C. with a reactor in which the circulation is maintained, it is observed that the conversion of the p-chloro-benzyl alcohol to p-chloro-benzaldehyde proceeds linearly during the first two hours and reaches a final conversion of 8% (5.10$^{-3}$ mols) with 100% selectivity to the aldehyde. At the end of the experiment the plates of titanium which have a residual quantity of $MnO_2$ are washed, dried with warm air, and are used as the anode in a 1M KOH solution at 25° C. with a current of 12 A (100 A/m$^2$) for a period of five minutes (the quantity of current being circulated is 37.10$^{-3}$ eq). The plates of titanium with the layer of $MnO_2$ which has been regenerated are washed, dried and caused to react with p-chloro-benzyl alcohol under the same conditions used previously with the exception of the temperature which is adjusted to 65° C. After two hours, the conversion reaches 24% (15.10$^{-'}$mols) with 100% selectivity with respect to the aldehyde. The test has been repeated recycling the plates of titanium covered with $MnO_2$ between the phase of electrolytic oxidation and the phase of chemical reaction, obtaining the same results. The average electric yield per cycle results to be about 80%. The electrical consumption results in the order of 1 KWh/kg of product.

When a certain amount of agitation is required, the entire electrode pack may be exposed to vibration or oscillation upwardly and downwardly by means of cams, elastic supports, etc. connected to the wall of the container and to the frame of the cathodic structure for the purpose of facilitating the exchanges of the material.

FIG. 2 shows a different embodiment in which the stage of oxidation or reduction of the organic substance takes place in a reactor which has a moving bed connected to an installation of motion of the redox system which is supported on spherules from the chemical reactor to the electrochemical reactor, the latter also being on a moving bed. Several types of installations may be used, the only limitation residing in the electrical and mechanical properties of the redox system which is supported on the spherules and, in particular, the resistance to wear. There is described hereinbelow a workable installation in the case in which the redox system is ferromagnetic or when it is deposited on spheres of ferromagnetic material, for instance, ferritic stainless steel.

When an oxidation is being carried out the active mass may consist according to the various possible embodiments:

(1) of a surface layer of 1-100 μm deposited on metallic ferromagnetic spherules with a diameter of 0.5-5 mm;

(2) of a mass which impregnates the pores of plastic material in the form of a foam having open pores which has been carbonized by thermal cracking in a reducing atmosphere. In the center of the spherules of the foam of diameter between 5-50 mm, there is inserted a ferromagnetic nucleus. This embodiment is preferred when the redox system in the solid state is mechanically weak, particularly with respect to phenomena of wear (for instance, Ni(OH)$_2$/NiOOH).

The motion is achieved by means of magnetic plates which permit to limit to the maximum the phenomena of wear deriving from the rubbing of the spheres among themselves. FIG. 2 shows the installation in the form of a carousel connected with a magnetic plate with six working stations A-F.

FIG. 2a shows station A composed of electrolytic cell 17 with the electrolyte 18. The cathode 19 has a number of openings and is disposed at about the middle of the height of the cell. Numeral 20 designated the magnetic plate which may be moved. Numeral 21 designates the bottom of the cell which is made of metal and is connected to the anode. Anode and cathode are connected to the external generator of direct current which is not shown in the figure. Numeral 22 designates the magnetic spherules which have an active surface and which are transported above the cell with the magnetic plate and are allowed to fall through the openings of the cathode at the bottom. After the electrolysis is completed the spheres are brought back on the magnetic plate, are lifted above the level of the liquid and are freed of the electrolyte which has been held in the interstices.

Station B shown in FIG. 2b is the washing station: by means of the magnetic plate 20 the spheres 22 are allowed repeatedly to fall and to be raised in a suitable washing medium, for instance, distilled water. FIG. 2c illustrates the station C in which drying occurs by means of warm air: the spheres 22 are caused to move in the same manner as described hereinabove. FIG. 2d illustrates station D which serves as a reservoir for the spherules 22 already charged ready for the organic reaction. FIG. 2e illustrates station E which consists of the reactor in which the organic substrate 23 in the liquid or vapor form is oxidized on contact with the surface of the spheres. After the reaction is complete, the spheres may be brought back on the magnetic plate. FIG. 2f illustrates station F which is the washing station in a current of vapor used to remove from the surface of the spheres heavy products which may eventually have been deposited on them. (The vapor enters through the inlet 24 and exits through the outlet 25 carrying the organic substance present on the spheres 22. The condensate exits from exit 26.)

Figure 1A:
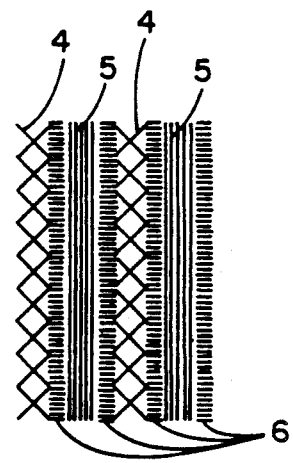

According to another embodiment, a reactor with a fixed bed such as the reactor shown in FIG. 1 is cyclically charged and discharged by means of a pump and automated valves with the several fluids required for the process: electrolytic solution, water for the washing, warm air for blowing through, the organic substance to be reacted, the product of the reaction, the solvent used for washing, and finally for vacuum distillation or steam distillation. The resulting system is capable of functioning cyclically in automatic fashion according to a suitably fixed program.

In the case in which an indirect electrochemical synthesis is being carried out on the cathode, the system which is utilized in the solid state is capable of accumulating by cathodic discharge hydrogen which is consumed in the organic reaction and which is then cathodically regenerated again during the phase of electrolysis. The remainder of the process follows the same procedure described hereinabove for the reaction occurring on the anode. As material suitable to accumulate hydrogen one may use a thin layer of palladium deposited on a metallic substrate, for instance, copper.

For the cathodic charge the surface is capable of accumulating 0.1 eq of hydrogen per m². By means of hydrides and other materials recently developed such as anodes on hydrogen for secondary batteries and particularly, alloys of nickel and lanthanum (LaNi$_2$ and similar material), and alloys of titanium and nickel (Hydrogen Energy System - Vol. 3, p. 1492—Proceedings of The 2nd World Hydrogen Energy Conference, Zurich, August 21-24, 1978) (U.S. Pat. No. 3,874,928, Apr. 1, 1975), one may accumulate substantial amounts of hydrogen in the order of 10 eq./m².

The electrolysis is carried out at room temperature with a solution of 10% NaOH containing traces of lead (10 mg/l) in order to increase the hydrogen overvoltage.

In view of the difficulty and the cost involved to obtain massive cathodes of Ni-La alloy, the material is used in the form of powder (typical dimension 1 μm) which is incorporated in a matrix of nickel obtained by galvanic deposition from a Watts bath (RaJ Narayan, "Reviews on Coating and Corrosion," Vol IV (2) p. 113, Freund Publishing House, Tel Aviv).

With a deposit of 30 g/m² of the alloy it is possible to accumulate 1 eq.H$_2$/m². As an example of the indirect electrochemical reduction on the cathode with a redox system in the solid state, an experiment has been carried out involving the reduction of benzalacetophenone to benzylacetophenone. There is used for the purpose of accumulating hydrogen a cathodic pack of copper coated with a thin layer of palladium. There is introduced into the reactor a solution of benzalacetophenone in ethyl acetate in the ratio of 1:7. The reaction carried out under normal pressure and room temperature proceeds according to the scheme:

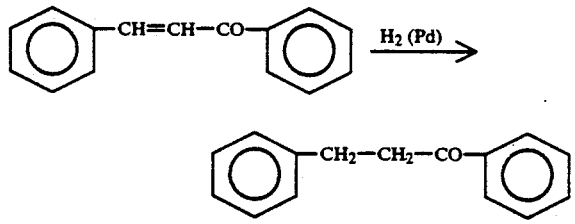

The benzylacetophenone formed in this manner, after distillation of the solvent, is recrystallized from ethyl alcohol. The yield is 80%.

What is claimed is:

1. A process of oxidation of an organic compound which comprises the steps of:
   1) subjecting to electrochemical oxidation in an electrolytic cell having an inert conducting support which conducts the electric current and containing an aqueous electrolyte, a solid oxide of a metal in a lower valence state, said metal having a higher valence state wherein the oxide of the metal in the higher valence state is deposited on said support in the solid form;
   2) interrupting the flow of electric current;
   3) removing said aqueous electrolyte from the electrolytic cell;
   4) introducing the organic compound to be oxidized into said electrolytic cell which serves as a reactor whereby said metallic oxide with the higher valence deposited on said inert support oxidizes said organic compound and said metal oxide is reduced to the oxide of the metal in the lower valence state while excluding the electric current from said reactor and cyclically repeating said steps 1), 2), 3) and 4).

2. The process according to claim 1 wherein said support is constituted by a metal and said metallic oxide in step 1) constitutes a surface layer of the oxide of said metal which serves as support.

3. A process according to claim 1 wherein said support is made of conducting plastic material or a plastic material which has been rendered conducting by pyrolysis.

4. The process according to claim 3 wherein said plastic material has a tri-dimensionally expanded structure.

5. The process according to claim 1 wherein said support has a geometric form and said geometric form has a planar surface.

6. The process according to claim 1 wherein said support is in the form of particles with a diameter comprised between 0.5 and 5 mm.

7. The process according to claim 1 wherein in step 1) said metallic oxide applied to said inert conducing support is contained in a reactor as a fixed bed and is placed in contact alternately with said aqueous electrolyte and with said organic compound to be oxidized.

8. The process according to claim 1 wherein said metallic oxide in the higher valence state present on the surface of said conducting support is washed with distilled water or with suitable solvent and is dried prior to step 4).

9. The process according to claim 1 wherein residues of the organic compound are formed in step 4) and metallic oxide of the metal in the lower valence state formed on said inert conducting support is subjected to elimination of the residues of the organic compound prior to repeating step 1).

10. The process according to claim 9 wherein said elimination of the residues is carried out by distillation under vacuum or by steam distillation.

11. The process according to claim 1 wherein at least one of said organic compound to be oxidized and the oxidized product is in the gaseous state.

12. The process according to claim 11 wherein the organic compound is in solution in a suitable solvent.

13. The process according to claim 1 wherein the organic compound to be oxidized is in suspension.

14. The process according to claim 1 wherein the support is made o titanium and the mixed oxide TiO$_2$-RuO$_2$ is thermally applied to said support.

15. The process according to claim 1 wherein said compound to be oxidized contains impurities which are oxidizable.

16. The process according to claim 1 wherein the oxide NiOOH/Ni(OH)$_2$ is galvanically applied to a nickel support.

17. The process according to claim 1 wherein the oxide NiCo$_2$O$_4$ is thermally applied to a support of titanium or nickel.

* * * * *